United States Patent [19]

Schaffer et al.

[11] 4,416,154

[45] Nov. 22, 1983

[54] METHOD FOR MEASURING THE SURFACE AREA OF A SOLID

[75] Inventors: Arnold M. Schaffer; Joseph G. Gallagher, Jr., both of Bartlesville, Okla.

[73] Assignee: Phillips Petroleum Company, Bartlesville, Okla.

[21] Appl. No.: 291,906

[22] Filed: Aug. 11, 1981

[51] Int. Cl.$^3$ ............................................. G01N 29/00
[52] U.S. Cl. ........................................ 73/571; 73/644
[58] Field of Search .................... 73/644, 571, 662, 24

[56] References Cited

U.S. PATENT DOCUMENTS 3,948,345  4/1976  Rosencwaig .......................... 181/0.5
4,028,932  6/1977  Rosencwaig .......................... 73/67.2
4,072,046  2/1978  Lao ....................................... 73/574

OTHER PUBLICATIONS

A. Rosencwaig and A. Gersho, "Theory of the Photoacoustic Effect with Solids", J. Appl. Phys. 47 (1) 64–69 (1976).

Bell, "Upon the Production of Sound by Radiant Energy", 1881, pp. 510–528, Philosophical Mag., vol. 11.

*Primary Examiner*—Anthony V. Ciarlante

[57] ABSTRACT

A method for enhancing the intensity of a photoacoustic signal by surrounding a solid with a gas having a normal boiling point at least about 25° C. below the temperature at which the photoacoustic effect is being measured and a critical temperature not less than about 2° C. By utilizing a second gas, selected from the permanent gases having a critical temperature not greater than about −73° C., the surface area of a solid can be measured in accordance with procedures and relationships herein described.

8 Claims, No Drawings

METHOD FOR MEASURING THE SURFACE AREA OF A SOLID

The invention relates to both a method for enhancing the intensity of a photoacoustic signal and a method for measuring the surface area of a solid. More particularly, it relates to a method for measuring the surface area of a porous solid by utilizing the photoacoustic effect.

This photoacoustic effect, discovered in 1880 by Alexander Graham Bell, can be seen by illuminating with intermittent light pulses a sample contained in a closed gas-filled cell and by measuring the resultant acoustic signals. Energy from the light pulses is converted by the sample to heat pulses which manifest themselves as sound waves in the coupling gas (i.e. the gas within the cell). The photoacoustic signal thus produced is proportional to the power of the radiation that is incident upon the sample. The signal can be detected by a microphone in the cell and, with suitable instrumentation, the signal's intensity can be measured quantitatively.

It is known that the intensity of a photoacoustic signal is proportional to the product of the ratio of the specific heats ($C_p/C_v$) of the coupling gas and the square root of the thermal diffusivity ($cm^2/sec$) of the coupling gas. Because these properties are sufficiently similar for nearly all gases, the nature of the coupling gas has not been considered to play a significant role in the production of the photoacoustic signal. It has now been found that by using certain coupling gases, the photoacoustic signal can be greatly enhanced over the result predicted by the above stated relationship. This is particularly so when the sample in contact with the coupling gas is a solid having a considerable surface area per unit weight.

It is also known that the intensity of a photoacoustic signal is proportional to the surface area of the sample. Since the intensity is sensitive to how a sample is loaded into a photoacoustic cell, no practical method has been described in the literature to use photoacoustic spectroscopy to measure surface area. A method has now been developed to measure surface area which eliminates the problems associated with sample loading. This technique is most suited for measuring the surface areas of supported catalysts on silica, alumina, titania, etc.

Accordingly, it is an object of this invention to provide a method whereby the intensity of a photoacoustic signal can be enhanced.

It is a further object of this invention to provide a method whereby the surface area of a solid can be determined by utilizing the photoacoustic effect.

These and other objects and advantages of the invention will become evident from the disclosure and claims to follow.

Gases that enhance photoacoustic signals are those which, by virtue of their volatility, are physically adsorbed to a substantial extent by the solid. These shall be referred to as the "higher boiling" gases. Higher boiling gases are those having normal boiling points at least about 25° C. below the temperature at which the photoacoustic effect is being measured and a critical temperature not less than about 2° C. Such higher boiling gases include ethane, ethylene, propane, propylene, n-butane, isobutane, isomeric butenes, ammonia, carbon dioxide and the like.

One aspect of this invention contemplates measuring the intensity of the photoacoustic signal emitted from a given sample for each of two different coupling gases. More particularly, it is contemplated that the intensity will be measured for both a higher boiling coupling gas and a lower boiling coupling gas. Measurements are preferably expressed as the ratio of these intensities (i.e. higher boiling to lower boiling).

Suitable "lower boiling" gases are the permanent gases having a critical temperature not greater than about −73° C. An additional desirable property is freedom from chemisorption or reaction with solids whose surface area is to be measured. The most preferred lower boiling gases are helium, neon, nitrogen and argon. Suitable, but less preferred, are hydrogen, oxygen, carbon monoxide and methane.

The method for measuring the surface area of solids through use of the photoacoustic effect is generally applied to finely divided solids, e.g., powders, etc. Before being placed in the photoacoustic cell they can be dried if they contain significant amounts of liquid. After they are in the cell measurements of photoacoustic signal intensity are taken, first in the presence of a higher boiling gas and then in the presence of a lower boiling gas. Alternatively, the lower boiling gas could be taken before the higher boiling gas. Allowing the proper gas to flow through the cell at a rate of about 5–10 changes of gas per minute for about 10 minutes provides adequate preparation for each measurement. The intensity of the photoacoustic signal corresponding to each gas is recorded. Results are expressed in terms of a ratio of one intensity to the other. For these measurements it is not necessary to illuminate the sample with monochromatic light since identical results are obtained with white light.

The measurement can be carried out at ambient temperature or any other convenient temperature (for example in an oven if an elevated temperature is desired).

At least two different procedures are available to convert the observed ratio of photoacoustic intensities to surface area. The first procedure refers the observed ratio to a calibration curve prepared under identicl conditions with a series of solids of known surface area. Calibration standards can be obtained from solids in which the surface area has been determined by the method of Brunauer, Emmett, and Teller, JACS 60, 309–319 (1938).

The second and preferable procedure obviates the need of preparing a calibration curve. Instead, the ratio of photoacoustic intensities corresponding to a sample of unknown surface area is compared to a similar ratio corresponding to a sample of known surface area. The ratio of surface areas of the two solids is directly proportional to the ratio of the two intensity ratios.

The method of this invention is applicable to all kinds of solids provided that they possess a considerable surface area. Generally the surface area should be at least about 10 square meters/gram and preferably should be at least about 50 square meters/gram. Exemplary solids include catalyst supports such as alumina, silica, silica-alumina, titania, zirconia, catalysts based on the above-mentioned materials but also containing other metals and oxides, finely divided metals such as metal "blacks" and the like.

The apparatus whereby the photoacoustic signal is measured is not considered to be a part of this invention. It comprises a light source, a chopper that converts the light beam to a pulsed source, a photoacoustic cell designed to permit the addition and removal of solids and also fitted to permit changing the coupling gas, a microphone, a preamplifier, a lock-in amplifier and a recorder. The apparatus depicted in U.S. Pat. No.

3,948,345, with a cell modified as suggested, is considered to be suitable. U.S. Pat. No. 3,948,345 is hereby incorporated by reference.

EXAMPLE 1

The invention was demonstrated with the use of three alumina samples of known surface area. The lower boiling coupling gas was nitrogen. Proprene and butane were used as higher boiling coupling gases. Results appear in Table I and are expressed in each instance of a ratio of observed photoacoustic intensities (i.e. higher boiling to lower boiling).

TABLE I

|  | Sample 1 | Sample 2 | Sample 3 |
|---|---|---|---|
| Alumina S.A., m$^2$/g | 90 | 150 | 240 |
| $I_{C_3H_6}/I_{N_2}$ | 2.4 | 3.9 | 4.9 |
| $I_{C_4H_{10}}/I_{N_2}$ | 3.3 | 5.2 | 11.9 |

The data show that the photoacoustic signals are enhanced substantially by the higher boiling gas when compared to the lower boiling gas (i.e. all ratios are substantially greater than 1). The observed ratio is proportional to the surface area of the solid in the photoacoustic cell, therefore, by using the results for one alumina sample the surface area of another sample can be estimated. If, for example, the surface area of Sample 1 was unknown it could be estimated from the data as follows:

$$\text{Surface Area} = \frac{2.4}{3.9} (150 \text{ m}^2/\text{g}) = 92.3 \frac{\text{m}^2}{\text{g}}$$

The resuts will not always be this accurate but the method does provide a convenient means for obtaining a "ballpark" estimate of the surface area.

EXAMPLE II

Measurements of the photoacoustic effect with six different coupling gases on two different solids were made that demonstrate the effect that an extended solid surface has on the measurement. One solid was glassy carbon with a surface area less than 1 m$^2$/g. The other solid was a tungsten oxide on silica catalyst having a surface area greater than 100 m$^2$/g. Table II compares the observed photoacoustic effects and also demonstrates the anomalous results with the higher boiling gases. All ratios represent the photoacoustic intensity associated with the corresponding gas divided by the photoacoustic intensity associated with N$_2$ (accordingly all ratios for N$_2$ are expressed as 1).

The predicted ratio is the result obtained when the above described relationship of photoacoustic intensity to the specific heats and thermal diffusivity of the coupling gas is utilized.

TABLE II

| Gas | a | b | Predicted Ratio | Observed ratio Carbon disc | Observed ratio WO$_3$/SiO$_2$ |
|---|---|---|---|---|---|
| He | 1.66 | 2.72 | 3.69 | 3.66 | 2.10 |
| N$_2$ | 1.404 | 0.28 | 1 | 1 | 1 |
| CO$_2$ | 1.304 | 0.14 | 0.66 | 0.66 | 3.24 |
| C$_3$H$_6$ | 1.15 | 0.09 | 0.46 | 0.48 | 6.26 |
| NH$_3$ | 1.304 | 0.20 | 0.78 | 0.83 | 6.98 |
| C$_4$H$_{10}$ | 1.09 | 0.22 | 0.69 | Not Determined | 7.96 |

$^a$Ratio of specific heats (C$_p$/C$_v$) of gas
$^b$Gas thermal diffusivity (cm$^2$/sec)

It is seen that in the presence of a solid having a low surface area the observed results are nearly identical to the predicted values. In contrast, in the presence of a solid having a high surface area the higher boiling gases provide a much stronger photoacoustic signal than conventional theory would have predicted.

It is not intended that the invention be limited in any way by the specifics of the examples. These examples are merely illustrative of the best mode known to the inventors of practicing the invention. It is contemplated that the scope of the invention shall include all reasonable variations and modifications of the invention as it has been taught and set forth in this disclosure and the appended claims.

We claim:

1. A method for enhancing the intensity of a photoacoustic signal emitted from a solid comprising:
   (a) placing a solid in a photoacoustic measuring zone;
   (b) surrounding said solid with a coupling gas comprising a gas having a normal boiling point at least about 25° C. below the temperature at which the photoacoustic effect is being measured and a critical temperature not less than about 2° C.; and
   (c) causing photoacoustic signals to be emitted from said solid;
   wherein said solid has a surface area in excess of about 10 square meters/gram.

2. A method in accordance with claim 1 wherein said coupling gas is ethane or ethylene.

3. A method in accordance with claim 1 wherein said coupling gas is propane or propylene.

4. A method in accordance with claim 1 wherein said coupling gas is n-butane, isobutane or isomeric butenes.

5. A method in accordance with claim 1 wherein said coupling gas is ammonia or carbon dioxide.

6. A method for measuring the surface area of a solid having a surface area in excess of about 10 square meters/gram which comprises:
   (a) placing said solid in a photoacoustic measuring zone;
   (b) surrounding said solid with a coupling gas comprising a gas having a normal boiling point at least about 25° C. below the temperature at which the photoacoustic effect is being measured and a critical temperature not less than about 2° C.;
   (c) causing photoacoustic signals to be emitted from said solid;
   (d) measuring the intensity of said photoacoustic signals;
   (e) removing said coupling gas from said photoacoustic measuring zone;
   (f) surrounding said solid with a second coupling gas comprising a permanent gas having a critical temperature not greater than about −73° C.;
   (g) causing additional photoacoustic signals to be emitted from said solid;
   (h) measuring the intensity of said additional photoacoustic signals;
   (i) calculating a ratio of the intensity of said photoacoustic signals to the intensity of said additional photoacoustic signals;
   (j) repeating steps (a) to (i) using a second solid of known surface area; and
   (k) estimating the surface area of the first solid by making use of the following relationship:

$$SA_1 = (SA_2)(R_1/R_2)$$

where $SA_1$ is the surface area of the first solid, $SA_2$ is the known surface area of the second solid, $R_1$ is the ratio of intensities calculated in step (i) which corresponds to the first solid and $R_2$ is the ratio of intensities calculated in step (i) which corresponds to the second solid.

7. A method for measuring the surface area of a solid having a surface area in excess of about 10 square meters/gram which comprises:
(a) placing said solid in a photoacoustic measuring zone;
(b) surrounding said solid with a coupling gas comprising a gas having a normal boiling point at least about 25° C. below the temperature at which the photoacoustic effect is being measured and a critical temperature not less than about 2° C.;
(c) causing photoacoustic signals to be emitted from said solid;
(d) measuring the intensity of said photoacoustic signals;
(e) removing said coupling gas from said photoacoustic measuring zone;
(f) surrounding said solid with a second coupling gas comprising a permanent gas having a critical temperature not greater than about −73° C.;
(g) causing additional photoacoustic signals to be emitted from said solid;
(h) measuring the intensity of said additional photoacoustic signals;
(i) calculating a ratio of the intensity of said photoacoustic signals to the intensity of said additional photoacoustic signals;
(j) estimating the surface area of said solid by comparing the ratio of intensities calculated in step (i) to a calibration curve prepared from a series of solids of known surface area.

8. A method in accordance with claim 1, 2, 3, 4, 5, 6, or 7 wherein said solid has a surface area in excess of about 50 square meters/gram.

* * * * *